(12) United States Patent
Mottaiyan et al.

(10) Patent No.: US 8,954,140 B2
(45) Date of Patent: Feb. 10, 2015

(54) METHOD AND SYSTEM FOR DETERMINING QRS COMPLEXES IN ELECTROCARDIOGRAM SIGNALS

(71) Applicant: Samsung Electronics Co., Ltd., Gyeonggi-do (KR)

(72) Inventors: Sabarimalai Manikandan Mottaiyan, Tamil Nadu (IN); Saurabh Tyagi, Uttar Pradesh (IN)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/036,553

(22) Filed: Sep. 25, 2013

(65) Prior Publication Data

US 2014/0088450 A1    Mar. 27, 2014

(30) Foreign Application Priority Data

Sep. 27, 2012 (IN) .............. 3030/DEL/2012
Aug. 9, 2013 (KR) ............. 10-2013-0094514

(51) Int. Cl.
  *A61B 5/04*   (2006.01)
  *A61B 5/00*   (2006.01)
  *A61B 5/0408* (2006.01)
  *A61B 5/0456* (2006.01)

(52) U.S. Cl.
  CPC .......... *A61B 5/04012* (2013.01); *A61B 5/7203* (2013.01); *A61B 5/0408* (2013.01); *A61B 5/0456* (2013.01)
  USPC ........................................... 600/521; 600/300

(58) Field of Classification Search
  USPC ................................................ 600/300, 521
  See application file for complete search history.

(56) References Cited

U.S. PATENT DOCUMENTS

2008/0288493 A1* 11/2008 Yang et al. ................. 707/7

* cited by examiner

*Primary Examiner* — Nicole F Lavert
(74) *Attorney, Agent, or Firm* — Cha & Reiter, LLC.

(57) ABSTRACT

A system automatically detects peaks in signal by generating a zero-mean data sequence of the signal comprising a data sequence and filtering the zero-mean data sequence. The entropy of the filtered data sequence is determined and peaks are detected in the entropy data sequence.

32 Claims, 12 Drawing Sheets

METHOD AND SYSTEM FOR DETERMINING QRS COMPLEXES IN ELECTROCARDIOGRAM SIGNALS

CLAIM OF PRIORITY

This application claims the benefit under 35 U.S.C. §119(a) from an Indian patent application filed on Sep. 27, 2012 in the Indian Patent Office and assigned Serial No. 3030/DEL/2012 and under 35 U.S.C. §119(a) of a Korean patent application filed on Aug. 9, 2013 in the Korean Intellectual Property Office and assigned Serial No. 10-2013-0094514, the entire disclosure of each of which is hereby incorporated by reference.

BACKGROUND

1. Field of the Invention

The present invention concerns a signal processing system for peak detection in an electrocardiogram (ECG) signal processing and analysis system, for example.

2. Description of the Related Art

An electrocardiogram (ECG) waveform or signal includes a series of characteristic points conventionally designated by the letters P, Q, R, S, and T. The Q, R, and S portions of the wave when taken together are referred to as a "QRS complex". The R-wave of the QRS complex is the most prominent wave in each cardiac cycle of the ECG signal.

Therefore, an efficient automatic detection of time instants of R-peaks is important in various ECG signal processing applications, such as Heart Rate Variability (HRV) analysis, computer-aided cardiac diagnostic system, Fetal Heart Rate (FHR) monitor, heart sound detection, ECG-based biometric system, ECG compression system, cardiac event change detector, wireless medical body area network, remote cardiac patient monitoring system, and other ECG signal processing applications.

Different digital processing systems and methods implement methods for detecting R-peaks or QRS complexes. Such methods can include, for example, Digital Filter (DF), filter-banks, Geometrical Matching (GM), genetic algorithms, Hilbert Transform (HT), Higher-Order Statistics (HOS), Hidden Markov Model (HMM), Linear Prediction (LP), Maximum-a-Posteriori (MAP) estimation, matched filters, mathematical morphology, multi-scale mathematical morphology, 3M and Empirical Mode Decomposition (EMD), syntactical rules, neural networks, Support Vector Machine (SVM), Template Matching (TM), Two-pole recursive filter, Wavelet Transform (WT), Zero-Crossing (ZC), and various other methods.

Although the known methods described above are effective in detecting R-peaks in an ECG signal, the known methods may have compromised performance when processing wide QRS complexes, low-amplitude QRS complexes, negative QRS polarities, sudden changes in RR intervals, sudden changes in QRS amplitudes, sudden changes in QRS morphologies, sharp P/T waves, and various kinds of noise (or artifacts) including baseline wander, power-line interference, muscle artifacts, electrosurgical noise, and motion artifacts. A system according to invention principles addresses these deficiencies and related problems and provides a robust system for automatically determining time instants of R-peaks in a received or recorded signal.

SUMMARY

A system according to invention principles automatically detects and accurately determines time instants of peaks in a received or recorded, enhances QRS complexes (or large high slope regions) and suppresses small-amplitude high-frequency noises and artifacts of a received or recorded signal. The system smoothes an envelope of a processed signal comprising large local maxima corresponding to desired QRS complexes in a received or recorded signal. The system automatically detects peaks in a sampled data signal, by generating a zero-mean data sequence of the signal comprising a data sequence with a substantially zero value mean by subtracting a mean value from the signal. The system filters the zero-mean data sequence, determines entropy (e.g. Shannon entropy) of the filtered data sequence and detects peaks in the entropy data sequence. The system divides the signal into processing blocks; and processes the signal blocks by performing a mean subtraction of the signal to determine the zero-mean data sequence of the signal and the signal comprises a heart electrical activity representative signal.

In a feature, filtering the zero-mean data sequence further comprises, generating an over-complete transform matrix, wherein the over-complete transform matrix comprises a set of elementary functions of the signal; estimating a transformation coefficient for the set of elementary functions of the over-complete transform matrix; and filtering the zero-mean data sequence using the estimated transform coefficient and the signal comprises an ECG signal. The set of elementary functions of the signal comprises at least one column vector from at least one of an identity matrix, a cosine matrix, and a sine matrix and the at least one column vector of the identity matrix is used to extract high-frequency components of the signal and the at least one column vector of the at least one of cosine matrix and sine matrix is used to extract low-frequency components of the signal. The size of the at least one of cosine matrix and sine matrix is less than size of the identity matrix.

In a feature, determining the entropy of the filtered data sequence of the signal further comprises: performing an amplitude normalization of the filtered data sequence, performing an absolute operation on the normalized filtered data sequence, wherein the absolute operation is performed to transform a bipolar filtered data sequence into a unipolar filtered data of the signal, performing adaptive thresholding on the transformed data sequence of the signal, and determining the entropy of the thresholded data sequence of the signal. The absolute operation is performed using at least one of linear transformation and non-linear transformation and the system smoothes the determined entropy data sequence of the signal.

In another feature the system convolves the smoothed entropy data sequence of the signal, wherein the convolved data sequence of the signal comprises at least one of positive zero-crossing point and negative zero-crossing point; and detects at least one location of the negative zero-crossing point in the convolved data sequence of the signal. The system detects peaks in the entropy data sequence by deriving a signal having zero-level crossing points indicating locations of the peaks having a zero gradient in the entropy data sequence. The system uses the at least one detected location of the at least one negative zero-crossing point to automatically determine the peaks of the signal.

In a further feature, the system automatically detects peaks in a sampled data signal using a blocking and mean subtraction module configured to determine a zero-mean data sequence of the signal by subtracting a mean value from the signal. A sparsity filtering module filters the zero-mean data sequence of the signal. An envelope module computes entropy of the filtered data sequence of the signal; and an output detector module automatically detects peaks in the entropy data sequence of the signal. A blocking and mean subtraction module divides the signal into processing blocks; and the system processes the signal blocks processed using at least one electrode lead by performing a mean subtraction of the signal to determine the zero-mean data sequence of the signal. A sparsity filtering module further comprises a dictionary matrix generation module configured to construct an over-complete transform matrix, wherein the over-complete transform matrix comprises a set of elementary functions of the signal. A sparse coefficient estimation module configured to estimate a transformation coefficient for the set of elementary function of the over-complete transform matrix, wherein the sparsity filtering module is configured to use the estimated transform coefficient to filter the zero-mean data sequence of the signal. The set of elementary functions of the signal comprises at least one column vector from at least one of an identity matrix, a cosine matrix, and a sine matrix and the at least one column vector of the identity matrix is used to extract high-frequency components of the signal and the at least one column vector of the at least one of cosine matrix and sine matrix is used to extract low-frequency components of the signal. The size of the at least one of cosine matrix and sine matrix is less than size of the identity matrix.

In yet another feature a Gaussian filtering module convolves the smoothed entropy data sequence, wherein the convolved data sequence of the signal comprises at least one of positive zero-crossing points and negative zero-crossing points; and a zero-crossing detector module configured to detect at least one location of the negative zero-crossing points in the convolved data sequence. An output detector module uses the at least one detected location of the at least one negative/positive zero-crossing point to automatically determine peaks or troughs of the signal. The output detector module combines the detected peaks of the signal to reduce at least one of false positive detection and false negative detection and the system selects at least one filtering method based on at least one digital signal processing application.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This invention is illustrated in the accompanying drawings, throughout which like reference letters indicate corresponding parts in the various figures. The embodiments herein will be better understood from the following description with reference to the drawings, in which.

DETAILED DESCRIPTION

Figure 1:
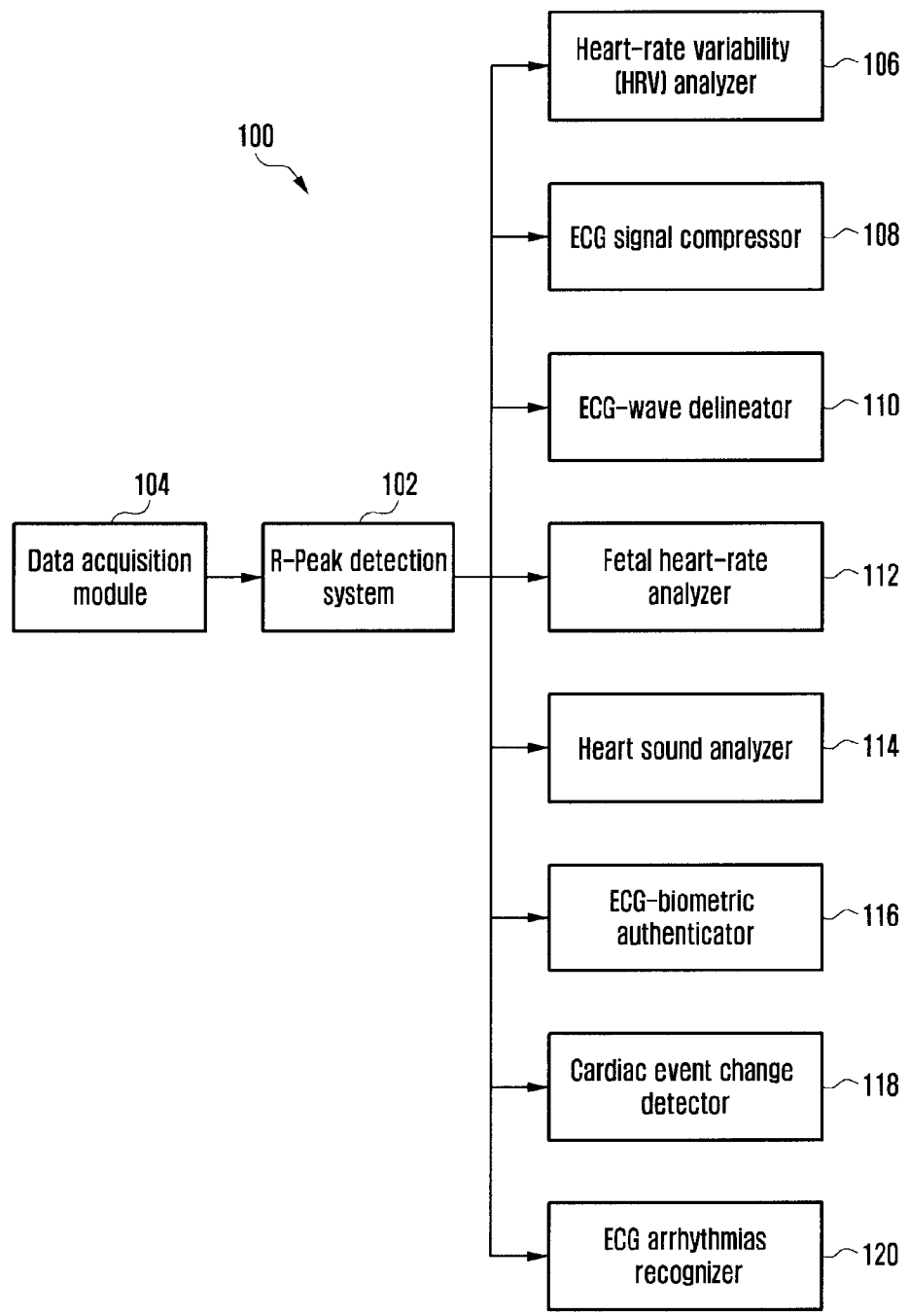
FIG. 1 shows a block diagram of applications of an R-peak detection system, according to invention principles.

The embodiments herein and the various features and advantageous details thereof are explained more fully with reference to the non-limiting embodiments that are illustrated in the accompanying drawings and detailed in the following description. For the purposes of clarity and simplicity, descriptions of well-known components and processing methods are omitted so as to not unnecessarily obscure the embodiments herein. The examples used herein are intended merely to facilitate an understanding of ways in which the embodiments herein can be practiced and to further enable those of skill in the art to practice the embodiments herein. Accordingly, the examples should not be construed as limiting the scope of the embodiments herein.

The system automatically determines time instants of R-peaks in a received or recorded signal using a sparsity filtering module to filter the signal and suppress baseline wander, power-line interference, muscle artifacts, motion artifacts, sharp P/T waves, and electrosurgical noises of the signal. An envelope module performs an amplitude normalization of the filtered data sequence of the signal. An absolute operation is performed on the normalized data sequence to transform a bipolar filtered data sequence into a unipolar filtered data sequence of the signal. The envelope module performs adaptive thresholding of the transformed data sequence and computes Shannon entropy of the thresholded data sequence of the signal. A signal as used herein comprises a digitally sampled signal representing heart electrical activity of a patient, for example, but in a different embodiment may also comprise an analog signal.

Further, the system employs a smoothing filter to remove noise from the computed Shannon entropy data sequence of the signal. A Gaussian filtering module convolves the smoothed Shannon entropy data sequence of the signal with a Gaussian derivative function. The Gaussian filtering module provides a convolved Shannon entropy data sequence that includes negative zero-crossing points indicating locations of R-peaks in the signal. A zero-crossing detector module detects the locations of the negative zero-crossing points in the convolved data sequence of the signal. An output detector module uses the detected locations to automatically determine the time instants of the R-peaks in the signal.

The system advantageously provides robust, reliable, inexpensive, and accurate detection of the R-peaks in a received or recorded signal under different noisy conditions. The system advantageously provides a one-pass detection method, without the use of search-back functions, using different amplitude-dependent and RR-interval-dependent thresholds. The system uses a single adaptive threshold rule to improve the accuracy of detecting the time instants of the R-peaks in the signal under different noisy conditions and uses automated peak-finding logic to accurately detect low-amplitude QRS complexes and wide-QRS complexes.

Referring now to the drawings, and more particularly to FIGS. 1 through 12, where similar reference characters denote corresponding features consistently throughout the figures, there are shown preferred embodiments.

Throughout the description, the terms sparsity filtering and L1-Sparsity filtering are used interchangeably. Throughout the description, the term dictionary matrix and transform matrix (or representation matrix or sparse matrix) are used interchangeably. The dictionary matrix can be overcomplete or undercomplete or critical depending on applications. Throughout the description, the terms elementary functions and elementary waveform (or basis functions or elementary atoms or elementary waveforms) are used interchangeably. Throughout the description, the terms transform coefficient and coefficient vector are used interchangeably.

FIG. 1 shows a block diagram 100 of applications of an R-peak detection system 102. The physiological conditions of a patient are monitored by positioning electrodes on the patient body in specific locations. Different channels are used to monitor electrical activity from different horizontal and frontal planes. R-peak detection system 102 processes multi-channels (or multi-electrode leads) outputs received from the electrodes. The output of the electrodes includes, for example, cardiac related electrical signals such as electrocardiogram (ECG) waveform signals, pacemaker pulse signals acquired by the electrodes, or any other physiological parameter of the patient. The R-peak detection system 102 is configured to be coupled to a data acquisition module 104 to acquire the physiological signal output from the electrodes.

The data acquisition module 104 is configured to receive cardiac biopotentials of the patient. The R-peak detection system 102 is configured to receive the physiological signal using the data acquisition module 104. The R-peak detection system 102 is configured to automatically determine time instants of R-peaks of the signal. The determined time instants of the R-peaks can be used by different signal processing applications for further processing or analysis purposes. The signal processing applications include, for example, Heart-rate variability (HRV) analyzer 106, ECG signal compressor 108, ECG-wave delineator 110, Fetal heart-rate analyzer 112, Heart sound analyzer 114, ECG-biometric authenticator 116, Cardiac event change detector 118, and ECG arrhythmias recognizer 120.

R-peak detection system 102 supports connection and control for communication of electronic data with the signal processing applications. The signal processing applications can be wired or wirelessly connected to the R-peak detection system 102 using methods such as cellular networks, Radio-frequency identification (RFID), ZigBee, Bluetooth, Wi-Fi, Ultra-wideband (UWB), Worldwide Interoperability for Microwave Access (WiMax), wireless USB, wireless local area network, near field communications, or other methods. In an embodiment, the signal processing applications are embedded in the R-peak detection system 102 to use the determined time instants for further processing or analysis purposes.

Figure 2:
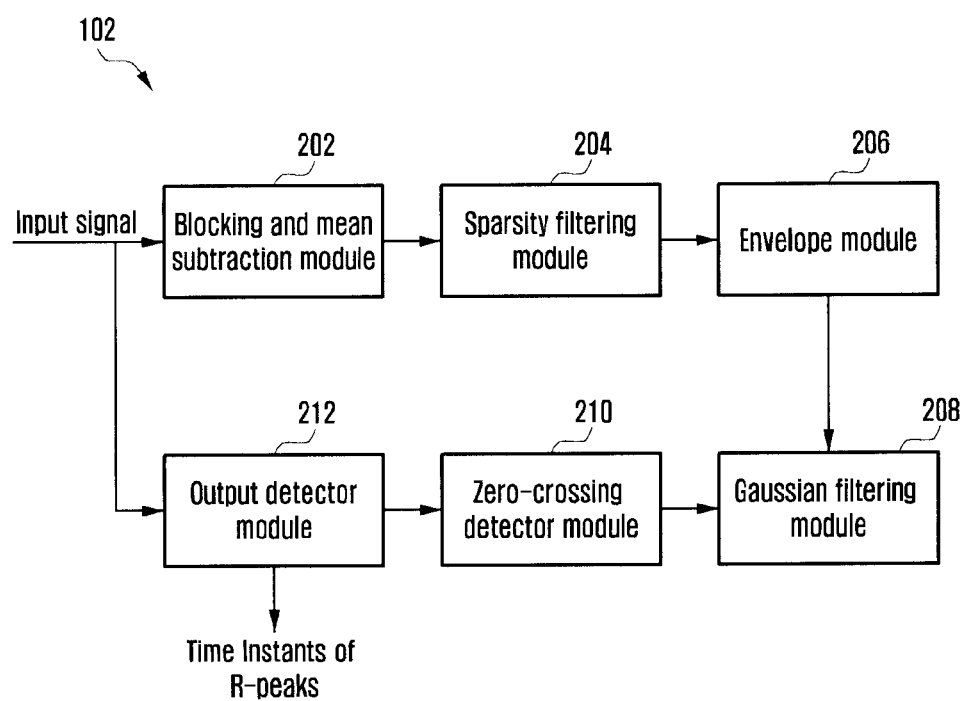
FIG. 2 shows more detail of the R-peak detection system of the FIG. 1, according to invention principles.

FIG. 2 shows R-peak detection system 102 of the FIG. 1 system including blocking and mean subtraction module 202, sparsity filtering module 204, envelope module 206, Gaussian filtering module 208, Zero-crossing detector module 210, and output detector module 212. The blocking and mean subtraction module 202 receives an ECG signal including cardiac biopotentials input from the data acquisition module 104 The blocking and mean subtraction module 202 divides the input signal into non-overlapping blocks of length N with certain time duration (for example, 10 seconds). The blocking of the input signal is performed for effective suppression of different shapes of the baseline wander. Further, the blocking and mean subtraction module 202 is configured to perform a mean subtraction of the input signal to provide a zero-mean discrete-time data sequence of the input signal. The mean subtraction of the input signal is performed to improve estimation of a transform coefficient of the signal.

In an example, the sparsity filtering module 204 is coupled to the blocking and mean subtraction module 202, to receive the zero-mean discrete-time data sequence of the input signal. The sparsity filtering module 204 is configured to filter the zero-mean discrete-time data sequence to enhance QRS complex portions of the input signal. The sparsity filtering module 204 suppresses the baseline wander, power-line interference, muscle artifacts, motion artifacts, sharp P/T waves, electrosurgical noises, and other noise (or artifact) of the input signal. Further, the sparsity filtering module 204 implements a L1-sparsity filtering method to filter the input signal based on an over-complete set of elementary functions or waveforms.

The envelope module 206 is coupled to the sparsity filtering module 204, to receive the filtered data sequence of the input signal and computes entropy of the filtered data sequence of the input signal. The entropy described herein is Shannon entropy, for example but may comprise Kolmogorov entropy or another entropy. The R-peak detection system 102 computes Shannon entropy to improve accuracy of detecting the time instants of the R-peaks in the input signal with low-amplitude and wide QRS complexes. Further, the envelope module 206 computes the Shannon entropy of the input signal.

The Gaussian filtering module 208 is coupled to the envelope module 206, to receive the Shannon entropy data sequence of the input signal. The Gaussian filtering module 208 employs peak-finding logic to identify locations of peaks in the input signal. The Gaussian filtering module 208 convolves the Shannon entropy data sequence with a Gaussian derivative function to identify the R-peak locations of the input signal. The convolved data sequence of the input signal includes positive zero-crossing points and negative zero-crossing points and the negative zero-crossing points indicate locations of the R-peaks in the Shannon entropy data sequence of the input signal.

The zero-crossing detector module 210 is coupled to the Gaussian filtering module 208, to detect the locations of the negative zero-crossing points in the Shannon entropy data sequence. In an example, these locations are used to determine the time instants of the R-peaks in the data sequence of the input signal.

The output detector module 212 is coupled to the zero-crossing detector module 210 and employs the detected locations of the negative zero-crossing points (indicating the locations of the R-peaks) to automatically determine the time instants of the R-peaks in the input signal. Further, the output detector module 212 provides the determined time instants of the R-peaks to different signal processing applications (for further processing or analysis). Further, the output detector module 212 employs data derived from a sequence of detected R-peaks in order to reduce false positive and false negative of the input signal.

Figure 3:
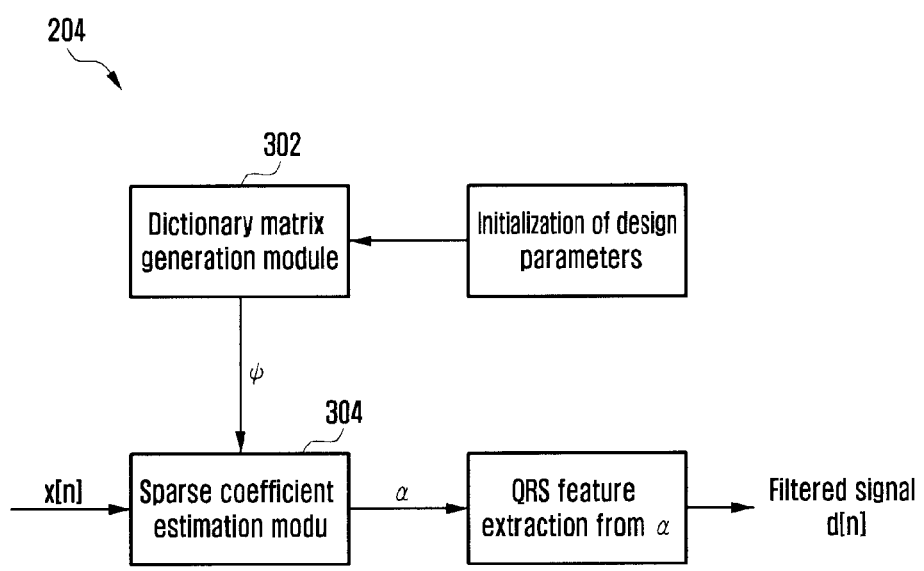
FIG. 3 shows a sparsity filtering module of the FIG. 2 system, according to invention principles.

FIG. 3 depicts a detailed view of the sparsity filtering module 204 of the FIG. 2 system. The sparsity filtering module 204 enhances the QRS complex portions and suppresses specific types of noise (or artifact) from a recorded or received signal. For this purpose, the sparsity filtering module 204 initiates design parameters including, an input signal (x[n]), a block length (N), a regularization parameter (λ), an over-complete transform matrix (Ψ), a Gaussian window length (P), and a rectangular window length (L). The blocking and mean subtraction module 202 divides the input signal x[n] into non-overlapping processing blocks of length N for effective suppression of different shapes of the baseline wander. The blocking and mean subtraction module 202 performs a mean subtraction of the input signal x[n] to provide a zero-mean discrete-time signal for better estimation of the transform coefficient (α) of the input signal x[n]. The sparsity filtering module 204 specifies a value to the regularization parameter to control fidelity and sparse constraint of the input signal x[n]. The Gaussian window is used to provide locations of peaks in the input signal x[n].

The sparsity filtering module 204 is configured to implement a L1-sparsity filtering method to filter the input signal x[n]. The method enhances the QRS complex portions and suppresses the baseline wander, power-line interference, muscle artifacts, motion artifacts, sharp P/T waves, and electrosurgical noises of the input signal x[n]. The sparsity filtering module 204 is configured, to include a dictionary matrix generation module 302, to generate or construct the over-complete transform matrix (Ψ) for the input signal x[n]. The dictionary matrix generation module 302 generates an under-complete or critical transform matrix for the input signal x[n]. The over-complete transform matrix (Ψ) includes a set of elementary functions from column vectors of an identity matrix (I) and a cosine matrix (C). The column vectors of the identity matrix (I) are used to extract high-frequency components of the input signal x[n] and the column vectors of the cosine matrix (c) are used to extract-low frequency components of the input signal x[n].

The dictionary matrix generation module 302 constructs the over-complete transform matrix $\Psi \in R^{N \times M}$ with size of N×M (where, N<M that contains M prototype waveforms for columns of ψ). The over-complete transform matrix (Ψ) includes a set of elementary functions from two matrixes, which is computed as Ψ=[I C], where I is the N×N identity matrix and C is the N×K cosine matrix. In an example, the input signal $x \in R^{N \times N}$ is represented as a linear combination of the prototype waveforms (as the column vectors={ψ$_1$|ψ$_2$|ψ$_3$| ... |ψ$_M$}):

$$x = \Psi \alpha = \sum_{m=1}^{M} \alpha_m \psi_m, \psi_m \in R^{N \times 1},$$

Where, α=[α$_1$, α$_2$, α$_3$, ... α$_M$] is the transform coefficients vector that is computed as α$_m$=⟨x,ψ$_m$⟩.

The transform coefficient (α) needs to be computed for the input signal x[n] and the over-complete transform matrix ψ. The sparsity filtering module 204 is configured, to include a sparse coefficient estimation module 304, to compute the transform coefficient (α) by using a L1-norm minimization algorithm. For the input signal x[n] and the over-complete transform matrix ψ, the transform coefficient (α) is computed by solving the following L1-norm minimization problem:

$$\hat{\alpha} = \underset{\alpha}{\operatorname{argmin}} \|\Psi \alpha - x\|_2^2 + \lambda \|\alpha\|_1$$

Where, $\|\Psi\alpha-x\|_2^2$ is fidelity term, $\|\alpha\|_1$ is a sparsity term, x is the input signal to be decomposed, and λ is the regularization parameter that controls the relative importance of the fidelity and sparseness terms.

In an example, for a pre-defined over-complete elementary function set ψ=[{i$_1$|i$_2$|i$_3$ ... i$_N$|c$_{N+1}$|c$_{N+2}$|c$_{N+3}$| ... c$_{N+K}$], the estimated transform coefficient (α) is given by $\hat{\alpha}=[\hat{\alpha}_1 \ \hat{\alpha}_c]$, where $\hat{\alpha}_1$ denotes the coefficients vector for the elementary functions from the column vectors of the identity matrix (I) and $\hat{\alpha}_c$ denotes the discrete cosine transform (DCT) coefficients vector for the elementary functions from the column vectors of the cosine matrix (C). The spike-like waveforms in the column vectors of the identity matrix $I \in R^{N \times N}$ can be used as a basis to extract QRS complex portions or high-frequency components of the input signal x[n]. The column vectors of the cosine matrix C∈RN×K can be used to extract the slowly-varying components or low-frequency components of the input signal x[n]. Further, the sparsity filtering module 204 is configured to filter the input signal x[n] by extracting the QRS complex portions from the transformation coefficient (α).

The filtered signal d[n] is computed as d=I$\hat{\alpha}_1$=$\hat{\alpha}_1$, where column vector $i_i \in R_{N \times 1}$ from the identity matrix (I) includes one non-zero entry. The output of the sparsity filtering module 204 is the filtered signal d[n] of the input signal x[n], which is further processed by the R-peak detection system 102 to locate the QRS complexes.

The R-peak detection system 102 configures sparsity filtering module 204 by selecting an appropriate filtering method from a, derivative filter, band-pass filter, wavelet decomposition, empirical mode decomposition, L1-sparsity filter, or another filtering method. The R-peak detection system 102 is configured to select the appropriate filtering method for enhancing QRS complex portions and reducing different types of noise and artifacts associated with the input signal. Depending upon the exemplary application(s) and computing resources requirements, the R-peak detection system 102 can implement the appropriate filtering method for the QRS detection.

Figure 4:
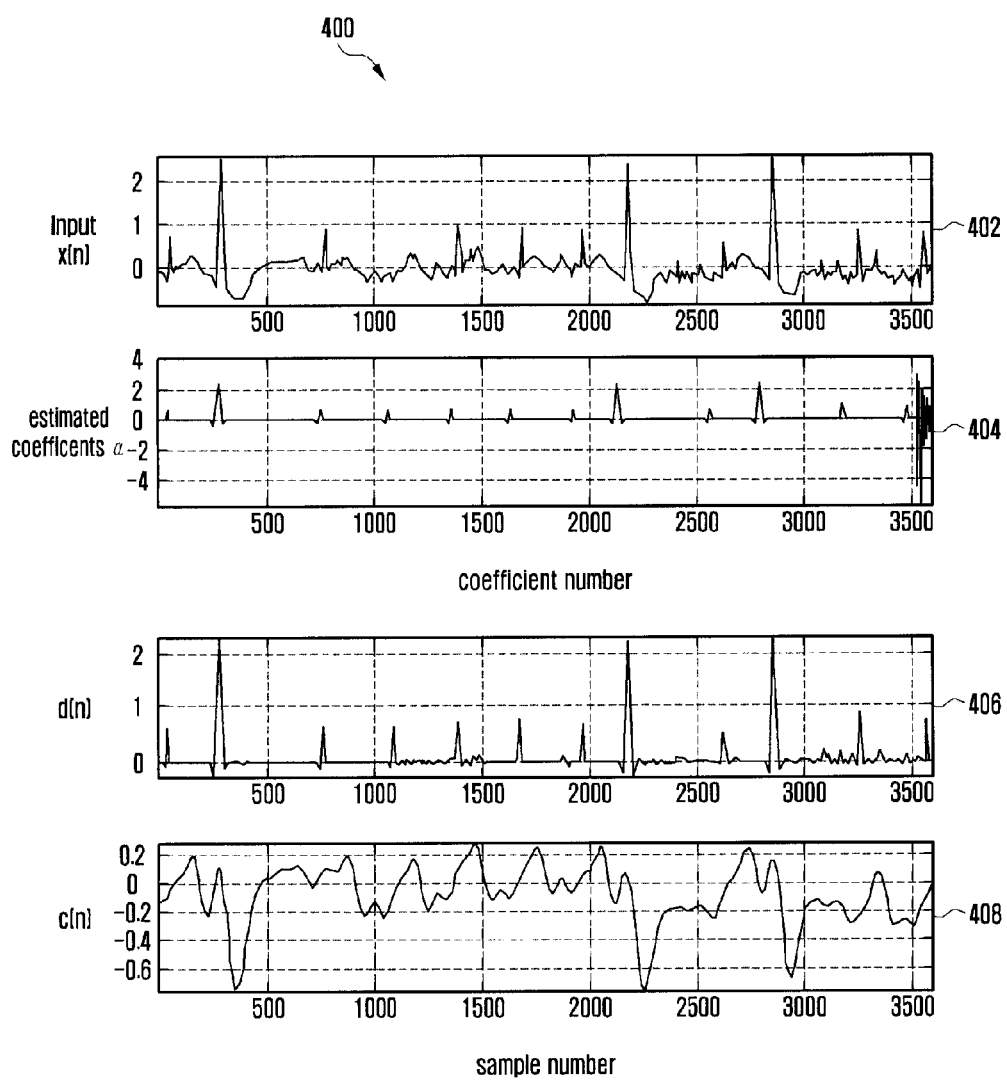
FIG. 4 shows graphs of experimental waveforms obtained by the sparsity filtering module of FIG. 3, according to invention principles.

FIG. 4 depicts graphs 400 representing an example of experimental waveforms obtained by the sparsity filtering module 204 of the FIG. 3. The performance of the L1-sparsity filtering method as described in the FIG. 3 is evaluated using an exemplary noisy or corrupted ECG signal 402. The estimated coefficients vector for the ECG signal 402 is shown in graph 404. The filtered signal d[n] is shown in graph 406. The filtered signal d[n] shows that the L1-sparsity filtering method emphasizes the QRS complex portions and simultaneously suppresses the baseline wander, power-line interference, muscle artifacts, motion artifacts, sharp P/T waves, and electrosurgical noises of the input signal x[n]. The low-frequency component constructed from the 77×1 discrete cosine transformed coefficients vector obtained for the discrete cosine functions is shown in graph 408. Thus, the experimental result shows that the spike-like waveforms from columns of the identity matrix (I) captures the QRS complex portions of the ECG signal 402.

Figure 5:
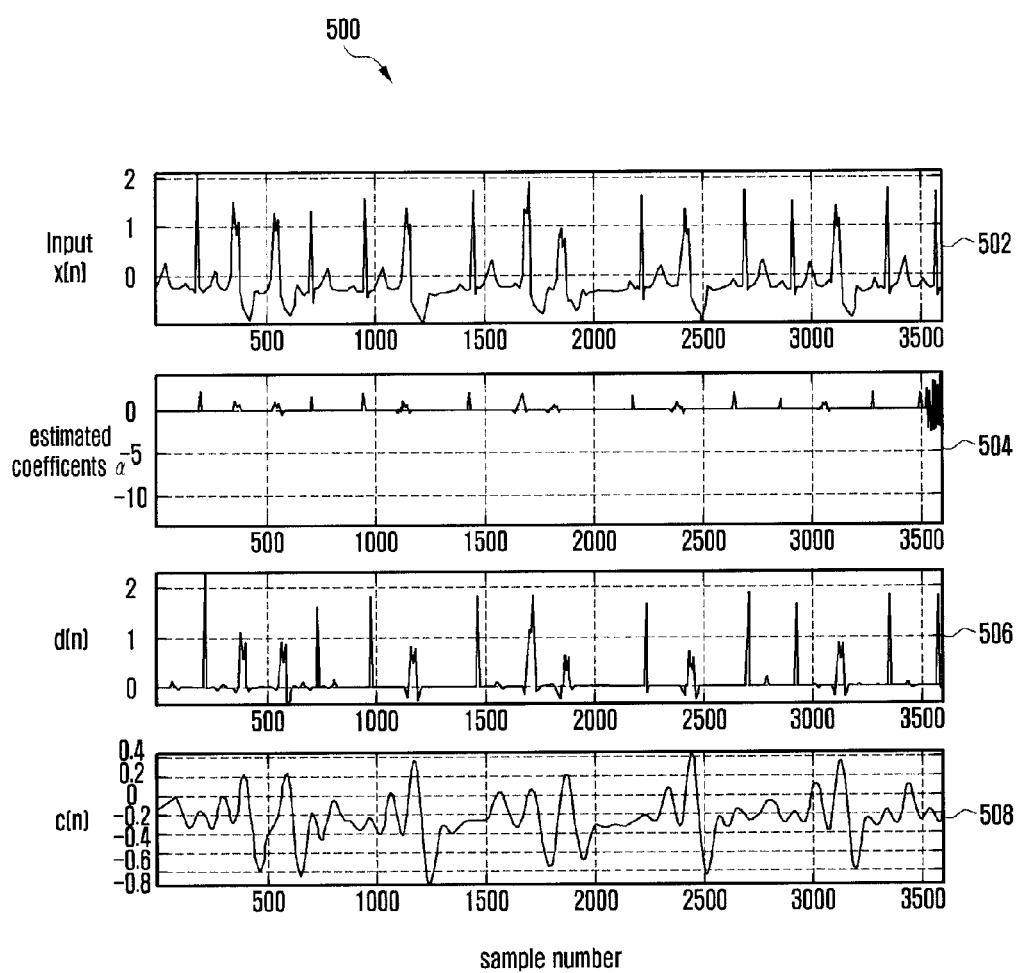
FIG. 5 shows graphs of experimental waveforms obtained by the sparsity filtering module of the FIG. 3, according to invention principles.

FIG. 5 depicts graphs 500 representing another example of experimental waveforms obtained by the sparsity filtering module 204 of FIG. 3. The performance of the L1-sparsity filtering method as described in the FIG. 3 is evaluated using an exemplary noisy or corrupted ECG signal 502. The estimated coefficients vector for the ECG signal 502 is shown in graph 504. The filtered signal d[n] is shown in graph 506. The filtered signal d[n] shows that the L1-sparsity filtering method emphasizes the QRS complex portions and simultaneously suppresses the baseline wander, power-line interference, muscle artifacts, motion artifacts, sharp P/T waves, and electrosurgical noises in the input signal x[n]. The low-frequency component constructed from the 77×1 discrete cosine transformed coefficients vector obtained for the discrete cosine functions of is shown in graph 508. Thus, the experimental result shows that the spike-like waveforms from columns of the identity matrix (I) captures the QRS complex portions of the ECG signal 502.

Figure 6:
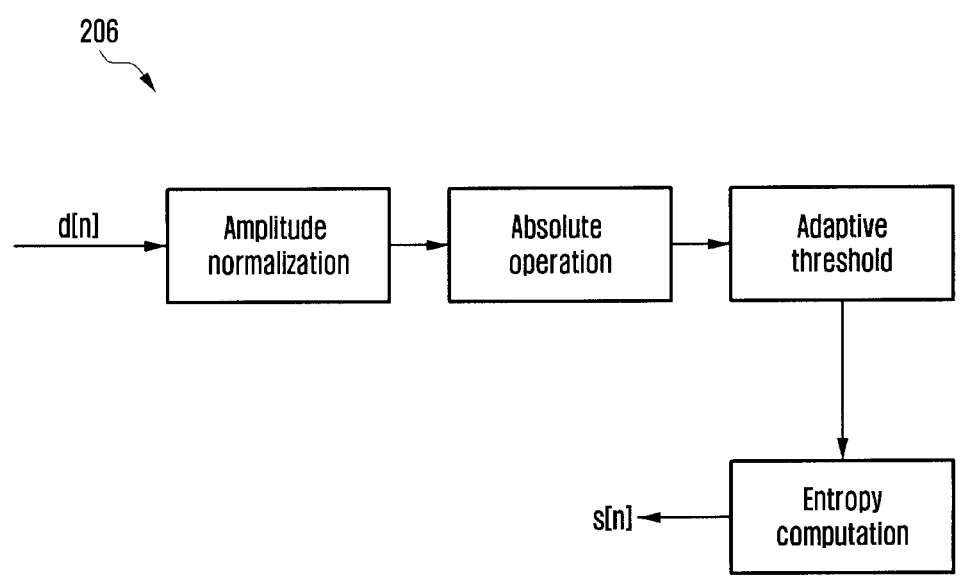
FIG. 6 shows an envelope module of the FIG. 2 system, according to invention principles.

FIG. 6 depicts a detailed view of the envelope module 206 of the FIG. 2. The envelope module 206 normalizes the filtered data sequence d[n] of the input signal x[n] in terms of peak amplitude. In an example, the normalization is achieved by multiplying the ECG waveform by normalization, or scaling, function. The amplitude normalization is performed using the following function:

$$\bar{d}[n] = \frac{d[n]}{\max_{n=1}^{N} |d[n]|}$$

The envelope module 206 performs an absolute operation on the normalized data sequence of the input signal x[n]. In an example, the envelope module 206 performs an absolute operation using a non-linear transformation method. The non-linear transformation is performed to convert a bipolar data sequence into a unipolar data sequence of the input signal x[n]. In an example, the non-linear transformation, including the absolute operation, is performed to convert the bipolar filtered ECG sequence into a positive-valued ECG sequence that eliminates detection problems in case of negative QRS complexes. The absolute value of the filtered data sequence d[n] is computed as:

$$a[n] = |\bar{d}[n]|$$

Further, the system converts the normalized data sequence of the input signal using a linear transformation method or a non-linear transformation method. The linear or non-linear transformation method includes an absolute operation, squaring operation, Shannon entropy operation, Shannon energy operation, or another method to obtain a positive-valued signal from the filtered signal that eliminates detection problems in the case of negative QRS complexes. The R-peak detection system 102 selects an appropriate linear or non-linear transformation operation based on peak-finding method, characteristics of noise components, computing resources, and level of detection accuracy required for targeted exemplary application(s).

The R-peak detection system 102 computes the amplitude normalization and the absolute operation as logic to reduce the computational complexity of the system 102.

The envelope module 206 performs adaptive thresholding on the transform data sequence of the input signal x[n]. In an example, the R-peak detection system 102 determines the applicability of thresholding function based on the filtering method used. The thresholding function is:

$$\tilde{a}[n] = \begin{cases} 0, & a[n] < \eta \\ a[n], & \text{elsewhere} \end{cases}$$

Where the absolute values a[n] is smaller than a threshold parameter η and the threshold parameter is set to zero. In an embodiment, the adaptive-threshold parameter η is computed for each input signal processing block. The threshold parameter η is determined based on the standard deviation of the absolute values of the normalized filtered data sequence of the input signal x[n]. The threshold process effectively eliminates spurious noise spikes and reduces the number of false positive detections under noisy ECG signals and ECG signal with long pauses.

The envelope module 206 is configured to compute the Shannon entropy of the thresholded data sequence of the input signal x[n]. The envelope module 206 implements a Shannon entropy based method for producing small deviations for the successive local maxima. The Shannon entropy of the sequence is computed as s[n]=−ã[n] log(ã[n]).

Further, the R-peak detection system 102 is configured to remove noise from the computed Shannon entropy data sequence s[n] of the input signal x[n]. In an example, the thresholded absolute values are smoothed using the zero-phase filtering with a rectangular impulse response (or rectangular window) of length L. Generally, the L is approximately the same as duration of possible wider QRS complex. In an example, the average of lower and upper duration limits of QRS complex portions is considered based on the length L of the rectangular window. The smoothing process reduces the effect of multiple peaks around QRS complex regions and provides sharp large local maxima around QRS complex portions. The smoothing process provides smoothed energy envelopes with isolated peaks corresponding to the QRS-complex portions in the input signal x[n]. The locations of the candidate R-peaks in the smoothed Shannon entropy data sequence s[n] correspond to approximate locations of the R-peaks in the input signal x[n].

The locations of peaks in the smoothed entropy data sequence s[n] are identified using the Gaussian filtering module 208 and the Zero-crossing detector module 210. The Gaussian filtering module 208 employs peak-finding logic to identify locations of peaks in the input signal. The Gaussian filtering module 208 provides an output sequence that is the convolution of the smoothed Shannon entropy s[n] with a Gaussian derivative kernel function g[n]. The output of the Gaussian filtering module 208 includes positive and negative zero-crossing points of the input signal x[n]. The negative zero-crossing points indicate locations of the peaks in the Shannon entropy data sequence s[n].

In an example, the P-point Gaussian window g[p] is computed as:

$$g[p] = e^{-\frac{1}{2}\frac{(p-\frac{P}{2})^2}{\sigma^2}} \quad p = 1, 2, 3 \ldots P$$

The first order Gaussian derivative sequence is computed as $g_d[p]=g[p+1]-g[p]$, p=1, 2, 3 ... P−1, which gives the slope at each sample.

The zero-crossing detector module 210 detects locations of negative zero-crossing points in the s[n] using the peak-finding logic. The output detector module 212 automatically determines the locations of true R-peaks in input signal x[n]. The output detector module 212 uses the detected locations of the negative zero-crossings (indicating the location of R-peaks) to automatically determine the time instants of the R-peaks in the input signal x[n]. In an example, the output detector module 212 combines the detection R-peaks to reduce the false positive and false negative detections of the input signal x[n]. Further, the output detector module 212 outputs the determined time instants of the R-peaks in the input signal x[n].

Further, the system uses different peak-finding methods to detect locations of negative zero-crossing points in the Shannon entropy data sequence. The peak-finding method may include a Hilbert-Transform (HT) and Moving Average (MA) filter, a first-order Gaussian differentiator, peak-amplitude thresholding and peak-searching window, or other peak-finding logic. The system detects peaks of P Q R waves within the received data by synchronization of a heart electrical activity waveform and peak detection of an R wave using a known peak detector and by identifying peaks of other waves by segmenting the signal represented by the sampled data into windows where the waves are expected and identifying the peaks within the windows. The Start point of an R wave, for example, is identified by a variety of known different methods. In one method the R wave start point comprises where the signal crosses a baseline of the signal (in a predetermined P wave window, for example). The baseline of the signal may comprise a zero voltage line if a static (DC) voltage signal component is filtered out from the signal. The R-peak detection system 102 selects an appropriate peak-finding method based on the computing resources and type of clinical procedure or application being performed.

Figure 7:
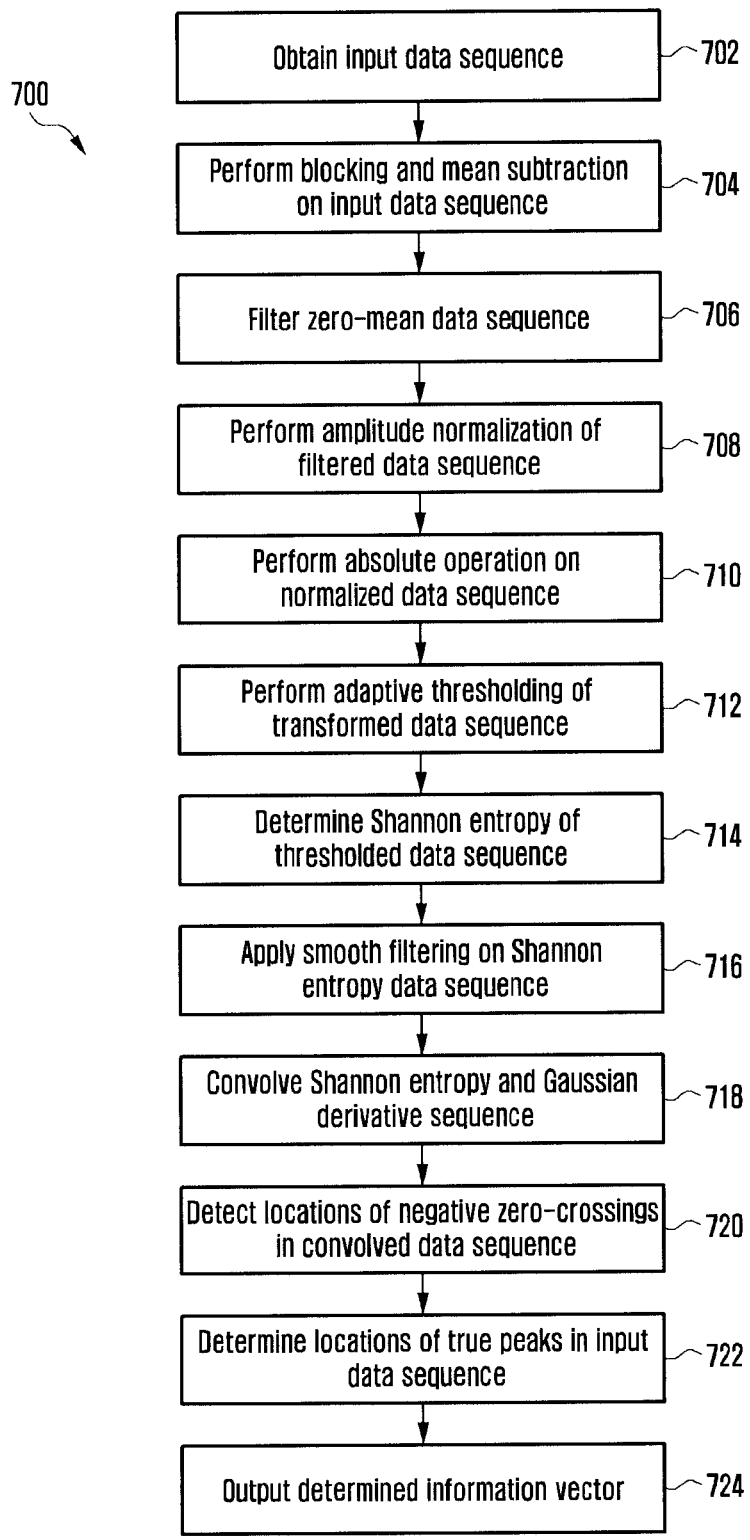
FIG. 7 shows a flow diagram illustrating operations performed by the R-peak detection system of the FIG. 2 system, according to invention principles.

FIG. 7 depicts a flow diagram 700 illustrating operations performed by the R-peak detection system 102 of the FIG. 2 system. At step 702, the R-peak detection system 102, in communication with the data acquisition module 104, receives an input data sequence x[n]. The input data sequence x[n] comprises an ECG signal including cardiac biopotentials, or another type of signal. The R-peak detection system 102 initializes the design parameters, for example, the input signal x[n], a block length (N), a regularization parameter (λ), an over-complete transform matrix (Ψ) a Gaussian window length (P), and a rectangular window length (L).

At step 704, the blocking and mean subtraction module 202 performs blocking and means subtraction on the input data sequence x[n]. The blocking and mean subtraction module 202 divides the input data sequence x[n] into non-overlapping processing blocks of length N for effective suppression of different shapes of the baseline wander. The blocking and mean subtraction module 202 performs a mean subtraction of the input data sequence x[n] to provide a zero-mean discrete-time data sequence for better estimation of the transform coefficient (α) of the input signal x[n].

At step 706, the sparsity filtering module 204 filters the zero-mean data sequence of the input signal x[n]. The sparsity filtering module 204 implements an L1-sparsity filtering method to enhance the QRS complex portions and suppress the baseline wander, power-line interference, muscle artifacts, motion artifacts, sharp P/T waves, and electrosurgical noises of the input data sequence x[n]. In an example, the sparsity filtering module 204, in communication with the dictionary matrix generation module 302, generates the over-complete transform matrix $\Psi \in R^{N \times M}$ with size of N×M (where, N<M that contains M prototype waveforms for columns of ψ) to filter the input data sequence x[n]. The over-complete transform matrix (Ψ) includes a set of elementary functions from two matrices computed as Ψ=[I C], where I is the N×N identity matrix and C is the N×K cosine matrix. In an example, the input data sequence $x \in R^{N \times 1}$ can be represented as a linear combination of the prototype waveforms as the column vectors=$\{\psi_1 | \psi_2 | \psi_3 \ldots | \psi_M\}$:

$$x = \Psi\alpha = \sum_{m=1}^{M} \alpha_m \psi_m, \psi_m \in R^{N \times 1},$$

In an example, the sparsity filtering module 204, in communication with the sparse coefficient estimation module 304, computes the transform coefficient (α) by using a L1-norm minimization algorithm. For the input data sequence x[n] and the over-complete transform matrix ψ, the transform coefficient (α) can be computed by solving the following L1-norm minimization problem:

$$\hat{\alpha} = \underset{\alpha}{\operatorname{argmin}} \|\Psi\alpha - x\|_2^2 + \lambda \|\alpha\|_1$$

In an example, the sparsity filtering module 204 filters the input signal x[n] by extracting the QRS complex portions from the transformation coefficient (α).

At step 708, the R-peak detection system 102 performs amplitude normalization of filtered data sequence d[n] of the input signal x[n]. The amplitude normalization is performed using the following function:

$$\bar{d}[n] = \frac{d[n]}{\max_{n=1}^{N} |d[n]|}$$

At step 710, the R-peak detection system 102 performs an absolute operation on the normalized data sequence of the input data sequence x[n]. A non-linear transformation, includes the absolute operation and is performed to convert a bipolar filtered data sequence d[n] into a unipolar data sequence of the input signal x[n]. The absolute operation is performed to eliminate detection problems in case of negative QRS complexes. The absolute value of the filtered data sequence d[n] is computed as a[n]=|d̄[n]|.

At step 712, the R-peak detection system 102 performs adaptive thresholding of the transformed data sequence of the input data sequence x[n]. The thresholding is performed to eliminate spurious noise spikes and to reduce the number of false positive detections of the input signal x[n]. The thresholding function comprises:

$$\tilde{a}[n] = \begin{cases} 0, & a[n] < \eta \\ a[n], & \text{elsewhere} \end{cases}$$

Where, the absolute values a[n] is smaller than a threshold parameter η. In an embodiment, the adaptive-threshold parameter η is computed for each input signal processing block. The threshold parameter η is chosen based on the standard deviation of the absolute values of the normalized filtered data sequence of the input signal x[n].

At step 714, the envelope module 206 determines Shannon entropy of the thresholded data sequence of the input signal x[n]. In an example, the envelope module 206 uses the Shannon entropy based method to produce small deviations for the successive local maxima of the input signal x[n]. The Shannon entropy of the sequence is computed as s[n]=−ā[n] log(ā[n]).

At step 716, the R-peak detection system 102 applies smooth filtering on the Shannon entropy data sequence s[n] of the input signal x[n]. The Shannon entropy data sequence s[n] is smoothed using zero-phase filtering with rectangular impulse response (or rectangular window) of length (L). The smooth filtering reduces the effect of multiple peaks around QRS complex regions and provides sharp large local maxima around QRS complex portions. The smooth filtering provides a smoothed Shannon entropy data sequence with isolated peaks corresponding to the QRS-complex portions in the input signal x[n].

At step 718, the Gaussian filtering module 208 convolves the smoothed Shannon entropy data sequence and first-order Gaussian derivative sequence. In an example, the Gaussian filtering module 208 convolves the smoothed Shannon entropy data sequence s[n] with a Gaussian derivative function g[n]. The output of the Gaussian filtering module 208 includes the positive and negative zero-crossing points of the input signal x[n]. The negative zero-crossing points indicate locations of the peaks in the Shannon entropy data sequence s[n].

At step 720, the zero-crossing detector module 210 detects the locations of the negative zero-crossings in the convolved data sequence of the input signal x[n].

At step 722, the output detector module 212 determines the locations of true peaks in input data sequence x[n]. The output detector module 212 uses the detected location of the negative zero-crossings (indicating the location of R-peaks) to automatically determine the time instants of the peaks in the input data sequence x[n]. The output detector module 212 uses data of a sequence of detected R-peaks to reduce false positive and false negative detections of the input signal x[n]. At step 724, the output detector module 212 outputs the determined information vector including the time instants of the peaks in the input data sequence x[n].

Figure 8:
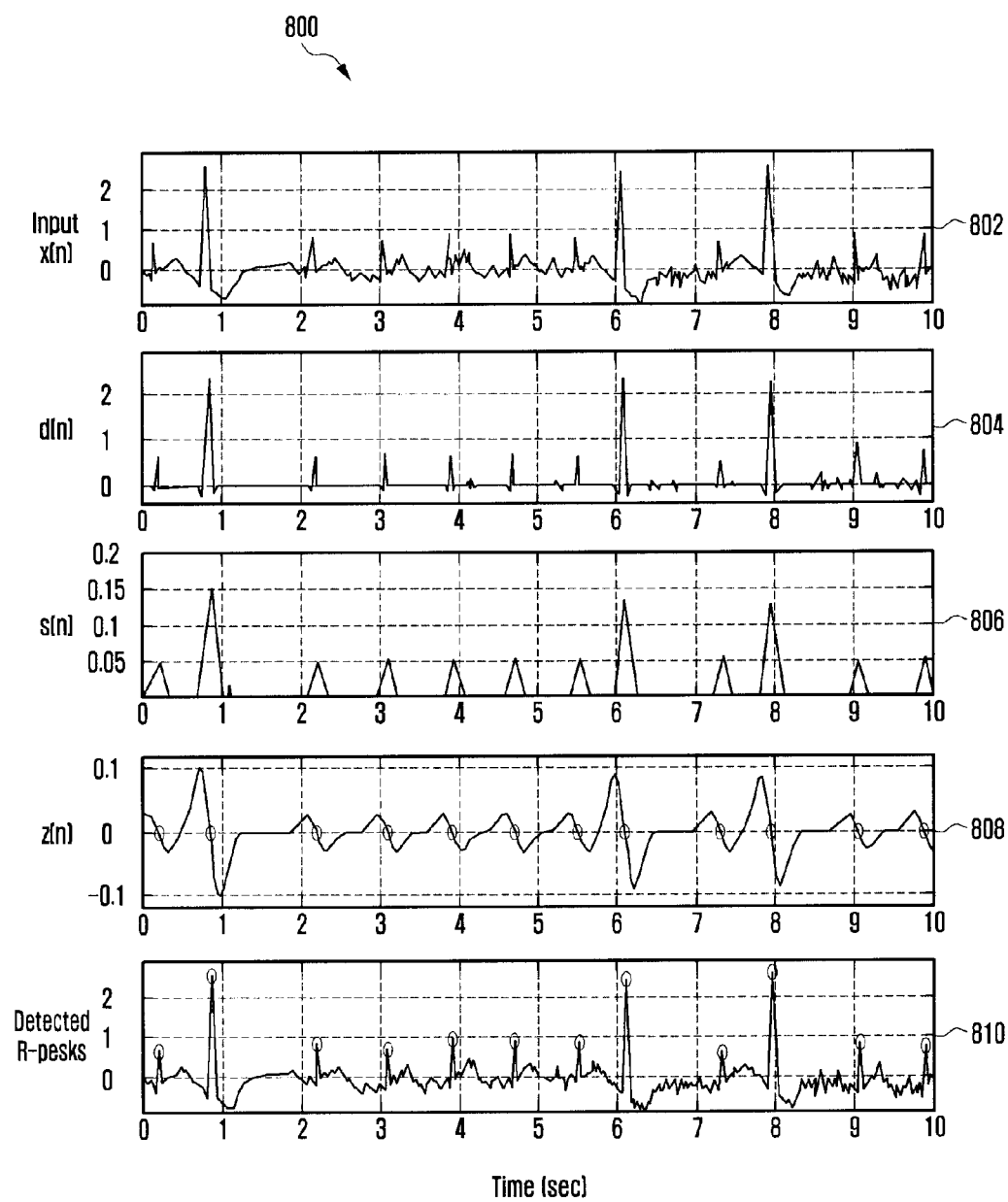
FIG. 8 shows graphs of experimental waveforms obtained by the R-peak detection system of the FIG. 2 system, according to invention principles.

FIG. 8 depicts graphs 800 representing an example of experimental waveforms obtained by the R-peak detection system 102 of the FIG. 2 system. The performance of the R-peak detection system 102 is evaluated using an exemplary noisy or corrupted ECG signal x[n] including low-amplitude QRS, narrow QRS, and wide QRS complexes is shown in graph 802. The filtered signal d[n] obtained using the sparsity filtering module 204 is shown in graph 804. The Shannon entropy data sequence s[n] obtained using the envelope module 206 is shown in graph 806. The output signal z[n] obtained using the Gaussian filtering module 208 is shown in graph 808. Graph 810 shows the detected R-peaks of the input signal x[n].

Figure 9:
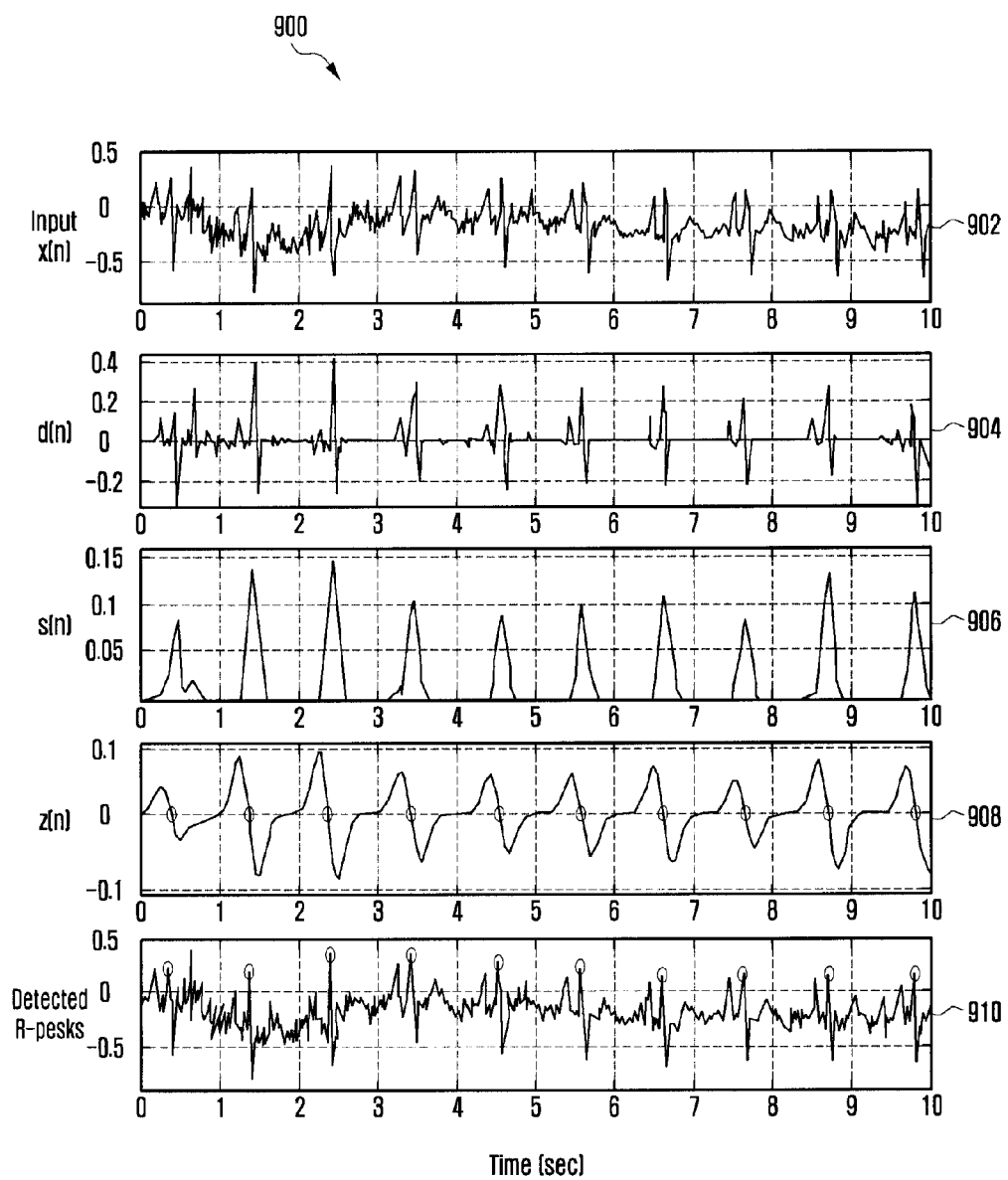
FIG. 9 shows graphs representing an example of experimental waveforms showing performance of detection of an ECG signal with large P-waves and muscle noise, according invention principles.

FIG. 9 depicts graphs 900 representing an example of experimental waveforms showing performance detection for ECG signal with large P-waves and muscle noise. An exemplary ECG signal x[n] including with large P-waves and muscle noise is shown in graph 902. The filtered signal d[n] obtained using the sparsity filtering module 204 is shown in graph 904. The Shannon entropy data sequence s[n] obtained using the envelope module 206 is shown in graph 906. The output signal z[n] obtained using the Gaussian filtering module 208 is shown the graph 908. Graph 910 shows the detected R-peaks of the input signal x[n]. The R-peak detection system 102 produces 07 false positive beats and 02 false negative beats for a total of 1763 true beats.

Figure 10:
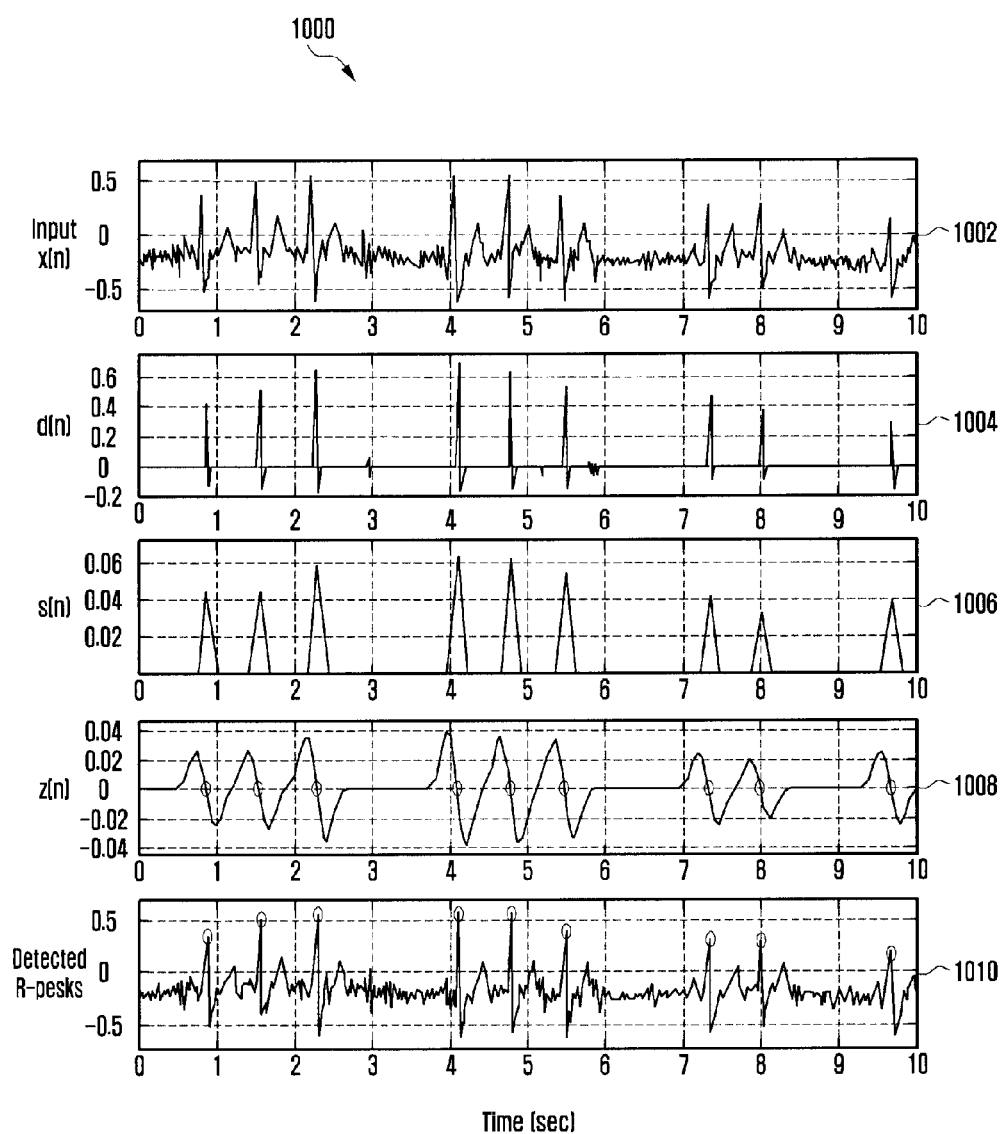
FIG. 10 shows graphs representing an example of experimental waveforms showing performance of detection of an ECG signal with noise and long pauses, according to invention principles.

FIG. 10 depicts graphs 1000 representing an example of experimental waveforms showing performance detection for ECG signal with noise and numerous long pauses. An exemplary ECG signal x[n] including noise and numerous long pauses up to 6 seconds is shown in graph 1002. The filtered signal d[n] obtained using the sparsity filtering module 204 is shown in graph 1004. The Shannon entropy data sequence s[n] obtained using the envelope module 206 is shown in graph 1006. The output signal z[n] obtained using the Gaussian filtering module 208 is shown in graph 1008. Graph 1010 shows the detected R-peaks of the input signal x[n]. The R-peak detection system 102 produces 02 false positive beats and 0 false negative beats for a total of 1780 true beats.

Figure 11:
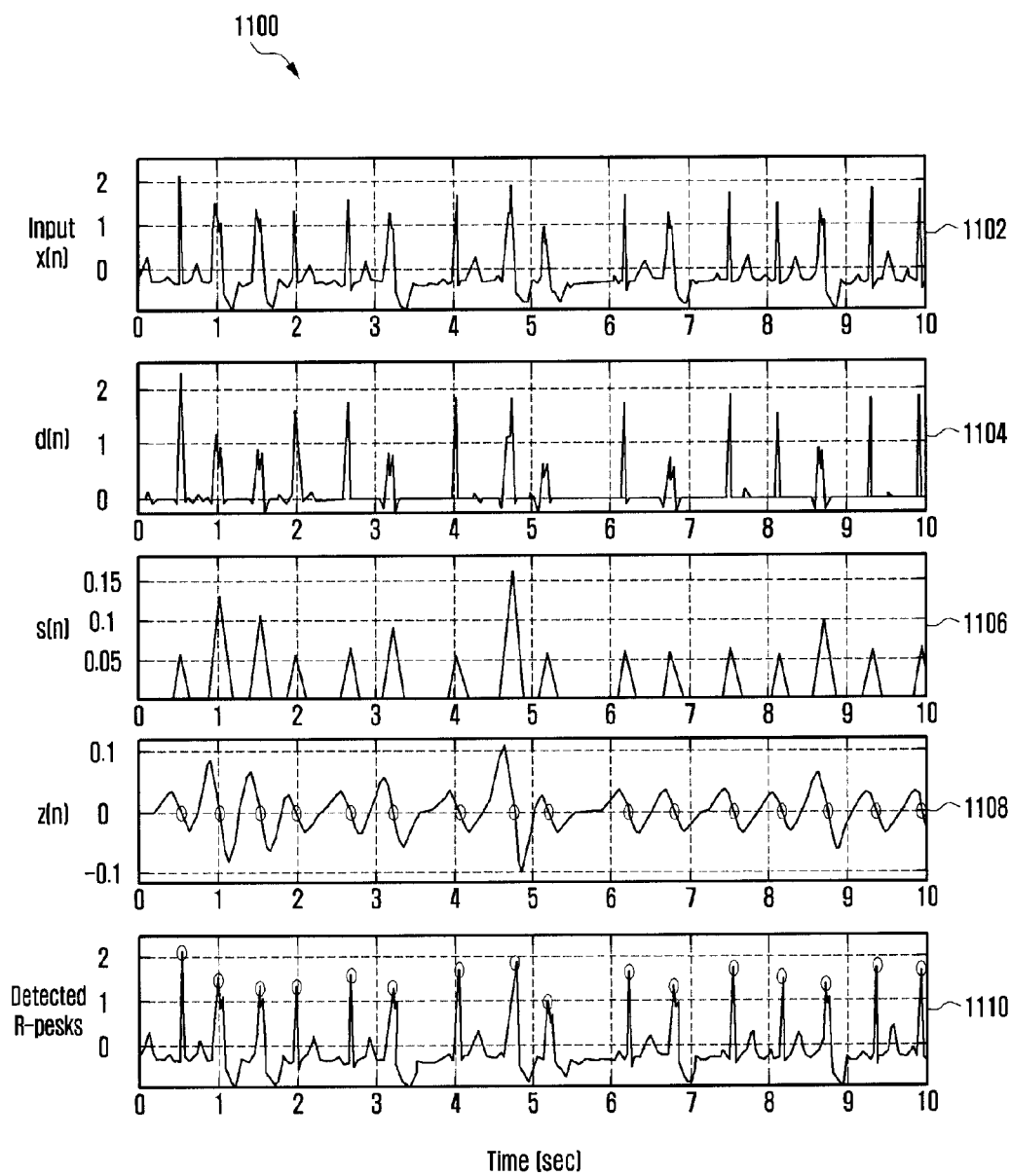
FIG. 11 shows graphs of experimental waveforms showing performance of detection of an ECG signal with wide QRS complexes, according to invention principles.

FIG. 11 depicts graphs 1100 representing an example of experimental waveforms showing performance detection for ECG signal with wide QRS complexes. An exemplary ECG signal x[n] including wide QRS complexes (premature ventricular contractions) is shown in graph 1102. The filtered signal d[n] obtained using the sparsity filtering module 204 is shown in graph 1104. The Shannon entropy data sequence s[n] obtained using the envelope module 206 is shown in graph 1106. The output signal z[n] obtained using the Gaussian filtering module 208 is shown in graph 1108. The detected R-peaks of the input signal x[n] is shown in Graph 1110. The R-peak detection system 102 produces 13 false positive beats and 0 false negative beats for a total of 2955 true beats.

The performance of the method and system is evaluated using the noisy ECG signals taken from the standard MIT-BIH arrhythmia database at "Moody G B, Mark R G, The impact of the MIT-BIH Arrhythmia Database", Moody G B, Mark R G. The impact of the MIT-BIH Arrhythmia Database. IEEE Eng in Med and Biol 20(3):45-50 (May-June 2001). (PMID: 11446209). The preliminary experimental results of the method are shown in FIGS. 4, 5, and 8-11. The visual inspection of the experimental results shows that the method automatically determines the time instants of R-peaks in an ECG signal. The results also shows that the method captures the QRS complex portions of the ECG signal and increases detection accuracy of R-peaks in an ECG signal.

Further, the experimental results shown in the below table illustrates that the system provides lower false positive and false negative detection rates in the terms of ECG signals with the sharp P/T waves, negative QRS complex, small QRS complex, wider QRS complex, muscle noise, baseline wander, power-line interference, baseline drift, sudden changes in QRS amplitudes, sudden changes in QRS morphology, multiform PVCs, long pauses, and irregular heart rhythms.

| Ref. no. | ECG Signal Quality | Total beats | EMD FP | EMD FN | MMM FP | MMM FN | Proposed FP | Proposed FN |
|---|---|---|---|---|---|---|---|---|
| 104 | multiform PVCs & severe muscle noise | 2229 | 16 | 05 | 07 | 01 | 08 | 00 |
| 105 | high-grade noise and artifacts | 2572 | 22 | 13 | 07 | 19 | 12 | 01 |
| 106 | abrupt changes in QRS morphology | 2027 | 00 | 05 | 21 | 20 | 01 | 02 |
| 108 | negative QRS & baseline drifts | 1763 | 12 | 15 | 10 | 02 | 07 | 02 |
| 113 | sharp-tall T waves | 1795 | 03 | 03 | 10 | 11 | 00 | 02 |
| 116 | very low-QRS (Amp. <0.05 mV) | 2412 | 10 | 07 | 04 | 27 | 00 | 16 |
| 203 | continuously varying QRS complexes | 2980 | 25 | 20 | 03 | 07 | 00 | 06 |

-continued

| Ref. no. | ECG Signal Quality | Total beats | EMD FP | FN | MMM FP | FN | Proposed FP | FN |
|---|---|---|---|---|---|---|---|---|
| 208 | wide-QRS & small-QRS <0.05 mV | 2965 | 13 | 06 | 03 | 10 | 00 | 13 |
| 223 | abrupt changes in amplitude of QRS | 2605 | 02 | 05 | 04 | 22 | 00 | 01 |
| 228 | abrupt changes in amplitude of QRS | 2053 | 11 | 19 | 10 | 02 | 06 | 02 |
| 232 | numerous long pauses up to 6 seconds | 1780 | 03 | 00 | 14 | 02 | 03 | 00 |
| | Total number of beats | 25171 | 119 | 98 | 93 | 123 | 37 | 43 |

Through the above description is described with respect to the ECG monitoring system, the person skilled in art can quickly identify that the invention can be used in other DSP systems. The present invention automatically detects time instants of peaks in a recorded or received signal and enhances quality of a signal and suppresses specific or complete noise or artifacts from a recorded or received signal.

Figure 12:
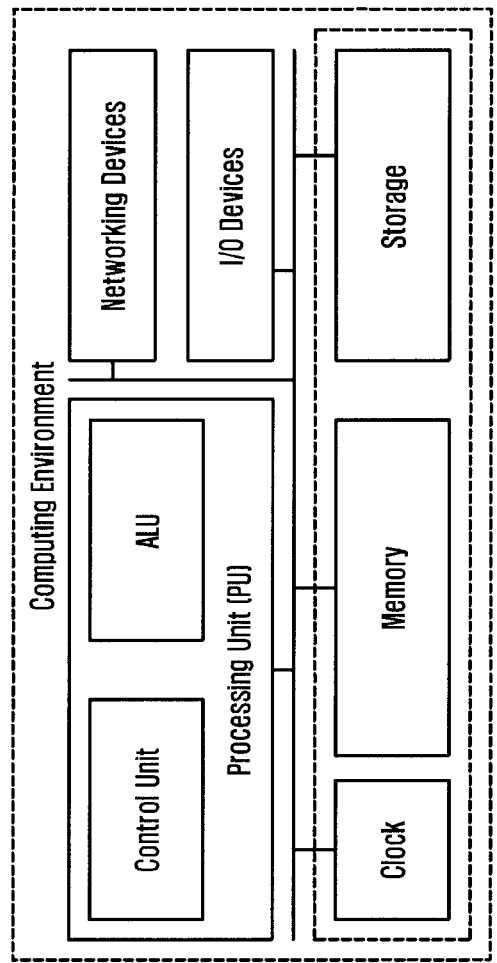
FIG. 12 shows a computing environment implementing the application, in accordance with invention principles.

FIG. 12 shows a computer implementing the application comprising at least one processing unit using a control unit and an Arithmetic Logic Unit (ALU), a memory, a storage unit, a clock chip, plurality of networking devices, and a plurality Input output (I/O) devices. The processing unit processes instructions of an algorithm in response to received commands from the control unit. Further, logical and arithmetic operations involved in the execution of the instructions are computed with the help of the ALU.

The overall computing environment comprises one or multiple homogeneous and/or heterogeneous cores, multiple CPUs of different kinds, special media and other accelerators. Further, the plurality of process units may be located on a single chip or over multiple chips.

The algorithm comprising instructions and codes is stored in either the memory unit or the storage or both. At the time of execution, the instructions may be fetched from the corresponding memory and/or storage, and executed by the processing unit. The processing unit synchronizes the operations and executes the instructions based on the timing signals generated by the clock chip. The embodiments disclosed herein can be implemented through at least one software program running on at least one hardware device and performing network management functions to control the elements. The elements shown in FIGS. 1-3, 6, and 7 include various units, blocks, modules, or steps described in relation with methods, processes, algorithms, or systems of the present invention, which can be implemented using any at least one of a general purpose processor, Digital Signal Processor (DSP), multi-core application processor, Graphics Processing Unit (GPU), Advanced RISC Machine (ARM) processor, multi-core processor or parallel processors, Field Programmable Gate Array (FPGA), Application Specific Integrated Circuit (ASIC), microcontroller, Software Defined Radio (SDR) tool, discrete hardware and analog circuit, and any combination of programming language, applications and embedded processor.

The above-described apparatuses and method can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. The functions and process steps herein may be performed automatically or wholly or partially in response to user command. An activity (including a step) performed automatically is performed in response to executable instruction or device operation without user direct initiation of the activity. No claim element herein is to be construed under the provisions of 35 U.S.C. 112, sixth paragraph, unless the element is expressly recited using the phrase "means for."

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

What is claimed is:

1. A method for automatically detecting peaks in a signal, the method comprising:
    subtracting a mean value from the signal such that a mean of the signal is substantially zero so as to generate a zero-mean data sequence; filtering the zero-mean data sequence; determining entropy of the filtered data sequence; and detecting the peaks in the entropy data sequence, wherein filtering the zero-mean data sequence further comprises: generating an over-complete transform matrix, wherein the over-complete transform matrix comprises a set of elementary functions of the signal; estimating a transformation coefficient for the set of elementary functions of the over-complete transform matrix; and filtering the zero-mean data sequence using the estimated transform coefficient.

2. The method of claim 1, wherein the method further comprises dividing the signal into processing blocks.

3. The method of claim 1, wherein the set of elementary functions of the signal comprises at least one column vector from at least one of an identity matrix, a cosine matrix, and a sine matrix.

4. The method of claim 3, wherein the at least one column vector of the identity matrix is used to extract high-frequency components of the signal.

5. The method of claim 3, wherein the at least one column vector of the at least one of cosine matrix and sine matrix is used to extract low-frequency components of the signal.

6. The method of claim 3, wherein size of the at least one of cosine matrix and sine matrix is less than size of the identity matrix.

7. The method of claim 1, wherein the entropy is Shannon entropy.

8. The method of claim 1, wherein determining the entropy of the filtered data sequence of the signal further comprises:
performing an amplitude normalization of the filtered data sequence,
performing an absolute operation on the normalized filtered data sequence, wherein the absolute operation is performed to transform a bipolar filtered data sequence into a unipolar filtered data of the signal,
performing adaptive thresholding on the transformed data sequence of the signal, and
determining the entropy of the thresholded data sequence of the signal.

9. The method of claim 8, wherein the absolute operation is performed using at least one of linear transformation and non-linear transformation.

10. The method of claim 1, wherein the method further comprises smoothing the determined entropy data sequence of the signal.

11. The method of claim 10, wherein the method further comprises:
convolving the smoothed entropy data sequence of the signal, wherein the convolved data sequence of the signal comprises at least one of positive zero-crossing point and negative zero-crossing point; and
detecting at least one location of the negative zero-crossing point in the convolved data sequence of the signal.

12. The method of claim 11, wherein detecting peaks in the entropy data sequence, comprises deriving a signal having zero-level crossing points indicating locations of the peaks having a zero gradient in the entropy data sequence.

13. The method of claim 11, wherein the method further comprises using the at least one detected location of the at least one negative zero-crossing point to automatically determine the peaks of the signal.

14. A system for automatically detecting peaks in a signal, the system comprising: a block and mean subtraction module configured to subtract a mean value from the signal such that a mean of the signal is substantially zero so as to generate a zero-mean data sequence; a sparsity filtering module configured to filter the zero-mean data sequence of the signal; an envelope module configured to compute entropy of the filtered data sequence of the signal;
and an output detector module configured to automatically detect peaks in the entropy data sequence of the signal, wherein the system further comprises a processor to select at least one filter method.

15. The system of claim 14, wherein the blocking and mean subtraction module is further configured to:
divide the signal into processing blocks.

16. The system of claim 14, wherein the signal is processed using at least one electrode lead.

17. The system of claim 14, wherein the sparsity filtering module further comprises:
a dictionary matrix generation module configured to construct an over-complete transform matrix, wherein the over-complete transform matrix comprises a set of elementary functions of the signal; and
a sparse coefficient estimation module configured to estimate a transformation coefficient for the set of elementary function of the over-complete transform matrix, wherein the sparsity filtering module is configured to use the estimated transform coefficient to filter the zero-mean data sequence of the signal.

18. The system of claim 17, wherein the set of elementary functions of the signal comprises at least one column vector from at least one of an identity matrix, a cosine matrix, and a sine matrix.

19. The system of claim 18, wherein the at least one column vector of the identity matrix is used to extract high-frequency components of the signal.

20. The system of claim 18, wherein the at least one column vector of the at least one of cosine matrix and sine matrix is used to extract low-frequency components of the signal.

21. The system of claim 18, wherein size of the at least one of cosine matrix and sine matrix is less than size of the identity matrix.

22. The system of claim 14, wherein the entropy is Shannon entropy.

23. The system of claim 14, wherein the envelope module is further configured to:
perform amplitude normalization of the filtered data sequence of the signal,
perform an absolute operation on the normalized filtered data sequence of the signal, wherein the absolute operation is performed to transform bipolar filtered data sequence into unipolar filtered data,
perform adaptive thresholding on the transformed data sequence of the signal, and
compute the entropy of the thresholded data sequence of the signal.

24. The system of claim 23, wherein the absolute operation is performed using at least one of linear transformation and non-linear transformation.

25. The system of claim 14, wherein the system further comprises a smoothing filter configured to filter noise from the computed entropy data sequence of the signal.

26. The system of claim 25, wherein the system smoothing filter is configured to perform zero-phase filtering on the transformed data sequence of the signal.

27. The system of claim 25, wherein the smoothing filter comprises a rectangular impulse response of length L.

28. The system of claim 25, wherein the system further comprises:
a Gaussian filtering module configured to convolve the smoothed entropy data sequence, wherein the convolved data sequence of the signal comprises at least one of positive zero-crossing points and negative zero-crossing points; and
a zero-crossing detector module configured to detect at least one location of the negative zero-crossing points in the convolved data sequence.

29. The system of claim 28, wherein the at least one negative zero-crossing point indicate locations of the peaks in the entropy data sequence of the signal.

30. The system of claim 28, wherein the zero-crossing detector module is configured to use peak-finding logic to detect at least one negative zero-crossing point in the convolved data sequence of the signal.

31. The system of claim 28, wherein the output detector module is configured to use the at least one detected location of the at least one negative/positive zero-crossing point to automatically determine peaks or troughs of the signal.

32. The system of claim 14, wherein the output detector module is further configured to combine the detected peaks of the signal to reduce at least one of false positive detection and false negative detection.

* * * * *